(12) United States Patent
Qi et al.

(10) Patent No.: US 11,759,162 B2
(45) Date of Patent: Sep. 19, 2023

(54) TOTAL SPECT SCATTER ESTIMATION AND CORRECTION USING RADIATIVE TRANSFER EQUATION

(71) Applicant: CANON MEDICAL SYSTEMS CORPORATION, Tochigi (JP)

(72) Inventors: Wenyuan Qi, Vernon Hills, IL (US); Yujie Lu, Vernon Hills, IL (US); Ryo Okuda, Tochigi (JP); Evren Asma, Vernon Hills, IL (US); Manabu Teshigawara, Tochigi (JP); Jeffrey Kolthammer, Vernon Hills, IL (US)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 81 days.

(21) Appl. No.: 17/345,716

(22) Filed: Jun. 11, 2021

(65) Prior Publication Data
US 2022/0395246 A1    Dec. 15, 2022

(51) Int. Cl.
*A61B 6/00*     (2006.01)
*A61B 6/03*     (2006.01)

(52) U.S. Cl.
CPC ............ *A61B 6/5282* (2013.01); *A61B 6/032* (2013.01); *A61B 6/037* (2013.01); *A61B 6/5205* (2013.01)

(58) Field of Classification Search
CPC ....... A61B 6/5282; A61B 6/032; A61B 6/037; A61B 6/5205
See application file for complete search history.

(56) References Cited

U.S. PATENT DOCUMENTS

| | | | |
|---|---|---|---|
| 8,090,431 B2* | 1/2012 | Wang .................... | A61B 6/508 600/425 |
| 8,428,692 B2* | 4/2013 | Wang .................. | A61B 5/0073 600/425 |
| 8,862,206 B2* | 10/2014 | Wang .................... | A61B 6/508 600/407 |
| 9,295,432 B2* | 3/2016 | Gerland ................. | A61B 6/542 |
| 10,200,655 B2* | 2/2019 | Kim ..................... | A61B 5/0073 |
| 10,271,811 B2* | 4/2019 | Lu ......................... | A61B 6/5282 |
| 10,593,070 B2* | 3/2020 | Lu ............................. | G06T 7/11 |
| 10,716,527 B2* | 7/2020 | Petschke .............. | A61B 6/4241 |
| 10,986,998 B2* | 4/2021 | Tichauer ............. | A61B 5/0071 |
| 11,060,987 B2* | 7/2021 | Lu ........................ | G01N 23/046 |
| 11,241,211 B2* | 2/2022 | Qi ......................... | A61B 6/032 |
| 11,276,209 B2* | 3/2022 | Qi ........................ | A61B 6/5205 |

(Continued)

OTHER PUBLICATIONS

Tereshchenko (Single-Photon Emission Computed Tomography in a Proportional Scattering Medium; ISSN 1063-7842, Technical Physics, 2017, vol. 62, No. 9, pp. 1293-1299). (Year: 2019).*

*Primary Examiner* — David P Porta
*Assistant Examiner* — Djura Malevic
(74) *Attorney, Agent, or Firm* — Oblon, McClelland, Maier & Neustadt, L.L.P.

(57) ABSTRACT

The present disclosure is related to removing scatter from a SPECT scan by utilizing a radiative transfer equation (RTE) method. An attenuation map and emission map are acquired for generating scatter sources maps and scatter on detectors using the RTE method. The estimated scatter on detectors can be removed to produce an image of a SPECT scan with less scatter. Both first-order and multiple-order scatter can be estimated and removed. Additionally, scatter caused by multiple tracers can be determined and removed.

20 Claims, 8 Drawing Sheets

(56) References Cited

U.S. PATENT DOCUMENTS

| | | | |
|---|---|---|---|
| 2004/0030255 A1* | 2/2004 | Alfano | A61B 5/415 600/476 |
| 2004/0249260 A1* | 12/2004 | Wang | A61B 6/508 600/407 |
| 2007/0093700 A1* | 4/2007 | Wang | A61B 5/0059 600/314 |
| 2007/0244395 A1* | 10/2007 | Wang | A61B 6/5247 600/476 |
| 2010/0310037 A1* | 12/2010 | Wang | A61B 6/06 378/87 |
| 2011/0060211 A1* | 3/2011 | Lorenzo | A61B 5/0073 600/425 |
| 2011/0184277 A1* | 7/2011 | Ripoll Lorenzo | A61B 5/0073 600/425 |
| 2011/0282181 A1* | 11/2011 | Wang | A61B 5/0095 600/407 |
| 2012/0069958 A1* | 3/2012 | Wang | G06T 11/005 378/63 |
| 2013/0108132 A1* | 5/2013 | Klose | G06T 7/0012 382/131 |
| 2014/0128730 A1* | 5/2014 | Wang | A61B 6/032 600/476 |
| 2014/0313305 A1* | 10/2014 | Kim | A61B 5/0073 348/77 |
| 2015/0265224 A1* | 9/2015 | Gerland | G16H 50/30 382/131 |
| 2015/0286785 A1* | 10/2015 | Hielscher | G06V 10/60 382/131 |
| 2016/0038029 A1* | 2/2016 | Darne | A61B 5/0071 600/427 |
| 2017/0148193 A1* | 5/2017 | Feng | A61B 5/7267 |
| 2017/0164835 A1* | 6/2017 | Wiest | G01S 15/8997 |
| 2018/0014806 A1* | 1/2018 | Lu | A61B 6/032 |
| 2018/0061031 A1* | 3/2018 | Rong | A61B 6/5258 |
| 2018/0204356 A1* | 7/2018 | Xia | A61B 6/582 |
| 2018/0235562 A1* | 8/2018 | Petschke | A61B 6/4241 |
| 2019/0197740 A1* | 6/2019 | Lu | A61B 6/4435 |
| 2020/0170601 A1* | 6/2020 | Gagnon | A61B 8/488 |
| 2020/0170607 A1* | 6/2020 | Yu | A61B 6/0487 |
| 2020/0234471 A1* | 7/2020 | Lu | G06T 7/11 |
| 2020/0340932 A1* | 10/2020 | Lu | G06N 20/00 |
| 2021/0282732 A1* | 9/2021 | Qi | A61B 6/5282 |
| 2021/0335023 A1* | 10/2021 | Qi | A61B 6/5205 |

* cited by examiner

TOTAL SPECT SCATTER ESTIMATION AND CORRECTION USING RADIATIVE TRANSFER EQUATION

BACKGROUND

Scatter is a substantial degrading factor in single positron emission computed tomography (SPECT) imaging. During imaging, photons emitted from a patient can scatter, leading to lower quality raw data and in turn, lower quality SPECT images. In most clinical situations, scattered photons can account for 30-40% of the photons detected in the photo-peak energy window of a SPECT scan. Thus, proper scatter correction can improve image quantification, lesion detection, signal to noise ratio, and more.

One commonly used technique for scatter correction in SPECT is the Triple Energy Window (TEW) method. This method uses measured scatter events in upper and lower energy windows on either side of a photo-peak window to predict scatter within the photo-peak window. The drawback of this technique is that is suffers from noise amplification due to poor statistics (i.e. few counts) from the necessarily narrow scatter photo-peak windows. Further, another limitation of the TEW method is that when dual or multiple tracer protocols are used, scatter estimation is confounded by different tracers' different energy distributions. As a result, the primary energy window for one tracer overlaps with the scatter window of other tracers, making scatter correction difficult when more than one tracer is used.

With the development of iterative maximum likelihood expectation maximization (ML-EM) reconstruction techniques, a system modelling multiple kinds of degrading factors can be included. A more accurate scatter modeling could improve the reconstruction. Though analytical calculations of scatter can be used, such a technique is very computationally-consuming. Further, due to the enormous computation power needed to run such as technique, analytical methods have been restricted to only first order scatter. Restricting to first order means that scatter from multiple-order scatter is ignored, which can account for approximately 10-20% of scatter in SPECT imaging. Other methods, such as Monte Carlo modelling, also suffer from very high computational costs. Therefore, in light of the previously mentioned problems, there exists a need for improved scatter correction techniques that are less computationally-consuming and can practically handle multiple-order scatter.

SUMMARY

The present disclosure is related to an apparatus for reconstructing an image in a single photon emission computed tomography (SPECT) scanner, comprising: processing circuitry configured to acquire an emission map and an attenuation map, the emission map and the attenuation map each representing an initial image reconstruction of an object of a SPECT scan, calculate, using a radiative transfer equation method, a scatter source map of the object of the SPECT scan based on the emission map and the attenuation map, estimate scatter using the radiative transfer equation method and based on the scatter source map, the emission map, the attenuation map, and SPECT scanner related information, and perform image reconstruction of the object based on the scatter and raw data from the SPECT scan of the object.

In one embodiment, the scatter source map includes contributions from first-order scatter and higher-order scatter.

In one embodiment, the scatter includes contributions from first-order scatter and higher-order scatter.

In one embodiment, the SPECT scanner related information includes position information of one or more detectors mounted on the SPECT scanner for scanning the object, and a collimator type of the one or more detectors, the collimator type being parallel or pinhole.

In one embodiment, the image reconstruction is performed iteratively.

In one embodiment, the image reconstruction is performed using filtered back projection.

In one embodiment, the attenuation map is based on a computed tomography scan of the object.

In one embodiment, multiple tracers are used in the object for the SPECT scan.

The present disclosure is also related to a method for reconstructing an image in a single photon emission computed tomography (SPECT) scanner, comprising: acquiring an emission map and an attenuation map, the emission map and the attenuation map each representing an initial image reconstruction of an object of a SPECT scan; calculating, using a radiative transfer equation method, a scatter source map of the object of the SPECT scan based on the emission map and the attenuation map; estimating scatter using the radiative transfer equation method and based on the scatter source map, the emission map, the attenuation map, and SPECT scanner related information; and performing image reconstruction of the object based on the scatter and raw data from the SPECT scan of the object.

In one embodiment, the scatter source map includes contributions from first-order scatter and higher-order scatter.

In one embodiment, the scatter includes contributions from first-order scatter and higher-order scatter.

In one embodiment, the SPECT scanner related information includes position information of one or more detectors mounted on the SPECT scanner for scanning the object, and a collimator type of the one or more detectors, the collimator type being parallel or pinhole.

In one embodiment, the image reconstruction is performed iteratively.

In one embodiment, the image reconstruction is performed using filtered back projection.

In one embodiment, the attenuation map is based on a computed tomography scan of the object.

In one embodiment, multiple tracers are used in the object for the SPECT scan.

The present disclosure is also related to a non-transitory computer-readable storage medium storing computer-readable instructions that, when executed by a computer, cause the computer to perform a method comprising: acquiring an emission map and an attenuation map, the emission map and the attenuation map each representing an initial image reconstruction of an object of a SPECT scan; calculating, using a radiative transfer equation method, a scatter source map of the object of the SPECT scan based on the emission map and the attenuation map; estimating scatter using the radiative transfer equation method and based on the scatter source map, the emission map, the attenuation map, and SPECT scanner related information; and performing image reconstruction of the object based on the scatter and raw data from the SPECT scan of the object.

In one embodiment, the scatter source map includes contributions from first-order scatter and higher-order scatter.

In one embodiment, the scatter includes contributions from first-order scatter and higher-order scatter.

In one embodiment, multiple tracers are used in the object for the SPECT scan.

DETAILED DESCRIPTION

The present disclosure describes using a radiation transfer equation (RTE) based approach to estimate scatter in SPECT. The described RTE method can achieve the same accuracy as related techniques in the field (e.g. Monte Carlo), be far less computationally consuming, account for multiple tracer energy distributions, and handle multiple-order scatter.

Simulating first- and multiple-order scatter flux can be done using RTE as follows:

$$\hat{\Omega} \cdot \nabla \psi(\vec{r}, E, \hat{\Omega}) + \mu(\vec{r}, E) \psi(\vec{r}, E, \hat{\Omega}) = \iint d\hat{\Omega}' dE' f(\vec{r}, E, E', \hat{\Omega} \cdot \hat{\Omega}') \psi(\vec{r}, E', \hat{\Omega}') + q(\vec{r}, E, \hat{\Omega}) \quad (1)$$

where the boundary condition is $\psi(\vec{r}_c, E, \hat{\Omega})=0$, for $\hat{n} \cdot \hat{\Omega}<0$; $\psi(\vec{r}, E, \hat{\Omega})$ is the specific intensity of photon flux at point $\vec{r}$, energy E, and direction $\hat{\Omega}$; $E'(\hat{\Omega}')$ and $E(\hat{\Omega})$ are the incident and outgoing energy (angle) of the flux; $q(\vec{r}, E, \hat{\Omega})$ is emission map, $\hat{n}$ is the normal direction of the boundary surface; and $f(\vec{r}, E, E', \hat{\Omega} \cdot \hat{\Omega}')$ is the scatter cross section.

An RTE method can be implemented for reconstructing an image in a SPECT scanner system. In one exemplary embodiment, the system comprises processing circuitry configured to: acquire an emission map and an attenuation map, the emission map and the attenuation map each representing an initial image reconstruction of an object of a SPECT scan; calculate, using a radiative transfer equation method, a scatter source map of the object of the SPECT scan based on the emission map and the attenuation map; estimate scatter using the radiative transfer equation method and based on the scatter source map, the emission map, the attenuation map, and SPECT scanner related information; and perform image reconstruction of the object based on the scatter and raw data from the SPECT scan of the object.

In one exemplary embodiment, the scatter source map includes contributions from first-order scatter as well as higher-order scatter (e.g. second-order scatter, third-order scatter). In one embodiment, the SPECT detector related information includes position information of the one or more detectors and a type of the one or more detectors, the type being parallel or pinhole collimated. In one exemplary embodiment, the image reconstruction can be performed iteratively, or, in another embodiment, be performed using filtered back projection. In one exemplary embodiment, the attenuation map is based on a computed tomography scan of the object. In another exemplary embodiment, the attenuation map is based off the emission map. In one exemplary embodiment, the emission map includes data obtained from multiple tracers.

Figure 1:
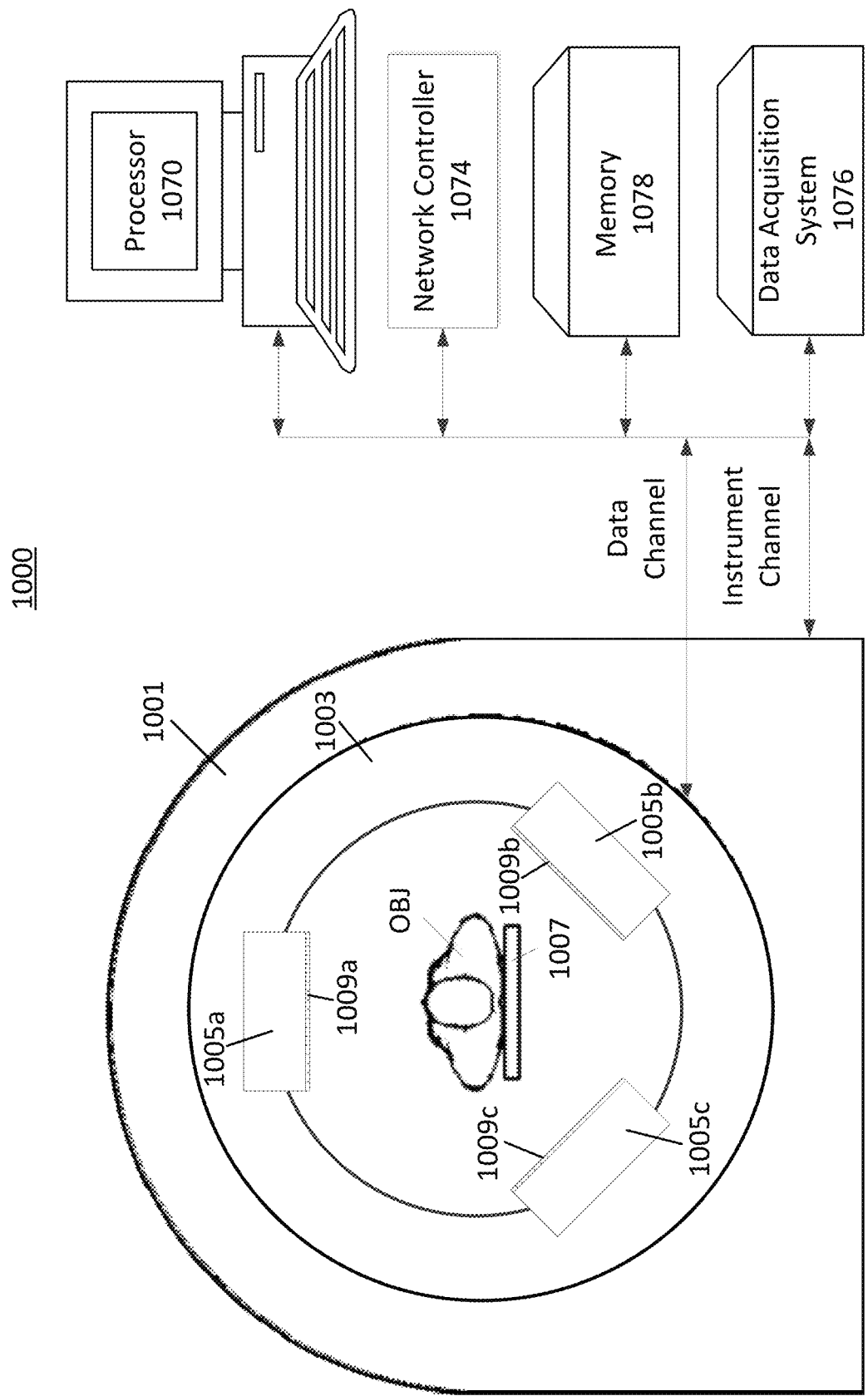
FIG. 1 is a schematic view of a SPECT scanner that can incorporate the techniques mentioned herein, according to one exemplary aspect of the present disclosure.

Referring now to the drawings, FIG. 1 shows a non-limiting example of a SPECT scanner 1000 system that can implement all or portions of method 300 (described later herein), method 600 (described later herein), and variations thereof. The SPECT scanner 1000 has a stationary gantry portion 1001 and a rotating gantry portion 1003. Detectors 1005a, 1005b, 1005c are mounted onto the rotating gantry portion 1003 for circularly rotating around an object OBJ (e.g. a patient) placed on the patient bed 1007 during SPECT scanning.

Each detector 1005a, 1005b, 1005c can include a two-dimensional array of individual detector crystals, which absorb gamma ray radiation and emit scintillation photons. The detectors 1005a, 1005b, 1005c have collimators (e.g. pinhole, parallel) 1007a, 1007b, and 1007c respectively for restricting the solid angle of gamma rays that could strike the detector crystals. The detector crystals can be scintillator crystals comprised of any know scintillating material. The scintillation photons can be detected by a two-dimensional array of photomultiplier tubes (PMTs) that are also arranged in the detectors. A light guide can be disposed between the array of detector crystals and the PMTs. Alternatively, the scintillation photons can be detected by an array a silicon photomultipliers (SiPMs), and each individual detector crystals can have a respective SiPM.

Each photodetector (e.g., PMT or SiPM) can produce an analog signal that indicates when scintillation events occur, and an energy of the gamma ray producing the detection event. Moreover, the photons emitted from one detector crystal can be detected by more than one photodetector, and, based on the analog signal produced at each photodetector, the detector crystal corresponding to the detection event can be determined using Anger logic and crystal decoding, for example.

In this implementation, the detectors 1005a, 1005b, 1005c are placed at 120 degree intervals about the object OBJ, and the rotating gantry portion 1003 rotates 120 degrees (clockwise or counterclockwise) about the object OBJ. In other implementations, more or less detectors may be placed in various other angular relations to one another. For example, two detectors can be positioned on opposite sides of the object OBJ, and the rotating gantry portion 1003 can rotate 180 degrees around the object OBJ. As another example, two detectors can be positioned orthogonally to each other, and the rotating gantry portion 1003 can rotate 360 degrees around the object OBJ.

The detectors 1005a, 1005b, 1005c and rotating gantry portion 1003 can be controlled automatically (e.g. by the processor 1070) or manually (e.g. by an operator) with a keyboard, mouse, display, and the like configured to the processor 1070. The rotation of the rotating gantry portion 1003 can be performed by a motor (e.g. DC motor, AC motor, stepper motor, hydraulic actuator), according to one exemplary embodiment.

Although not shown in this implementation, in another exemplary embodiment, the SPECT system 1000 can also be configured with an x-ray scanner system (e.g. SPECT/CT scanner) for obtaining x-ray data, such as an attenuation map.

Circuitry and hardware is also shown in FIG. 1 for acquiring, storing, processing, and distributing gamma ray radiation detection data. The circuitry and hardware include: a processor 1070, a network controller 1074, a memory 1078, and a data acquisition system (DAS) 1076. The SPECT system 1000 also includes a data channel that routes detection measurement results from the detectors 1005a, 1005b, 1005c to the DAS 1076, a processor 1070, a memory 1078, and a network controller 1074. The DAS 1076 can control the acquisition, digitization, and routing of the detection data from the detectors 1005a, 1005b, 1005c. In one implementation, the DAS 1076 controls the movement of the bed 1007. The processor 1070 performs functions including reconstructing images from the detection data, pre-reconstruction processing of the detection data, and post-reconstruction processing of the image data, as discussed herein.

The processor 1070 can be configured to perform various steps of method 300 and method 600 described herein, as well as variations thereof. The processor 1070 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, and may be provided to manage the electronic memory as well as the interaction between the FPGA or CPLD and the memory.

Alternatively, the CPU in the processor 1070 can execute a computer program including a set of computer-readable instructions that perform various steps of method 300, method 600, and variations thereof described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xeon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

The memory 1078 can be a hard disk drive, CD-ROM drive, DVD drive, FLASH drive, RAM, ROM or any other electronic storage known in the art.

The network controller 1074, such as an Intel Ethernet PRO network interface card from Intel Corporation of America, can interface between the various parts of the SPECT imager. Additionally, the network controller 1074 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

In one implementation, the reconstructed image can be displayed on a display. The display can be an LCD display, CRT display, plasma display, OLED, LED or any other display known in the art.

Figure 2A:
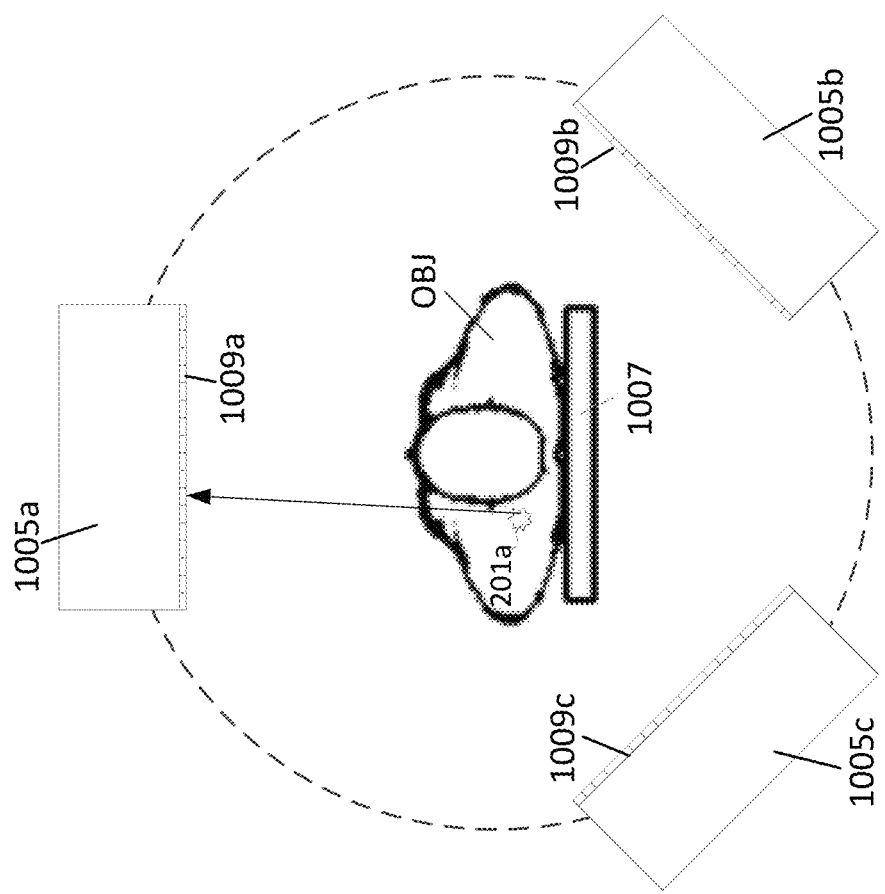
FIG. 2A shows zero-order scatter, according to one exemplary aspect of the present disclosure.
Figure 2B:
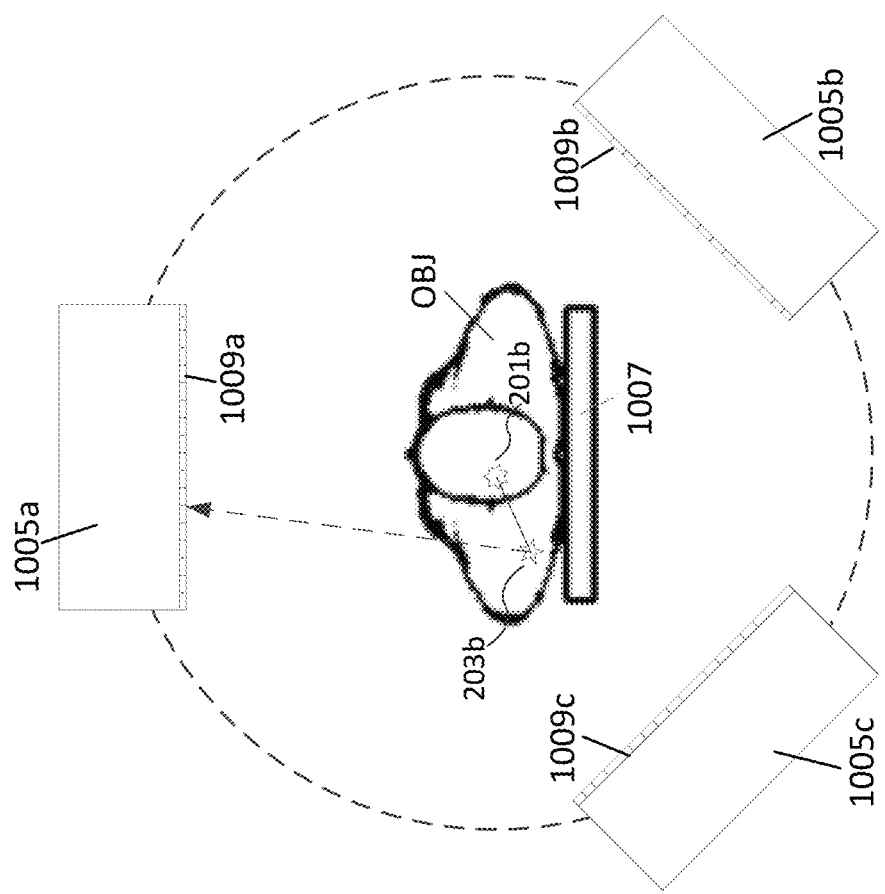
FIG. 2B shows first-order scatter, according to one exemplary aspect of the present disclosure.
Figure 2C:
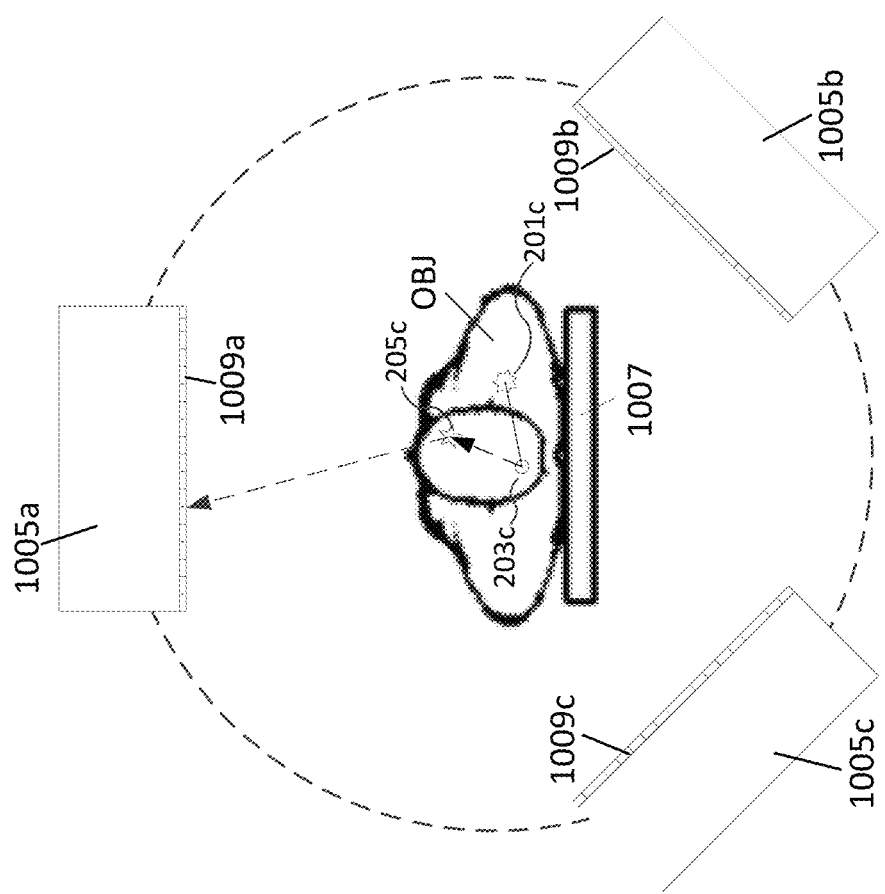
FIG. 2C shows multi-order scatter, according to one exemplary aspect of the present disclosure.

FIG. 2A through FIG. 2C visually illustrate gamma ray generation, scatter, and detection from zero-order events to higher-order events.

FIG. 2A shows an exemplary illustration of gamma ray detection in the absence of scatter. A gamma ray 201a is emitted from the object OBJ, passes through collimator 1009a on detector 1005a, and is detected within the detector's 1005a array of detector crystals and associated electronics.

In contrast, FIG. 2B shows an exemplary illustration of first-order scatter. A gamma ray 201b is emitted from the object OBJ, scatters at point 203b, and is eventually detected in detector 1005a.

FIG. 2C shows an exemplary illustration of higher-order scatter (i.e. more than one), which in this example is second-order scatter. A gamma ray 201c is emitted from the object OBJ, scatters at point 203c, scatters again at point 205c, and is eventually detected in detector 1005a and its associated electronics.

The SPECT scanner 1000 described above with respect to FIG. 1 may be configured in view of FIG. 2A through FIG. 2C to perform the methods described above and below with the reference to FIG. 3, FIG. 4, FIG. 5A, FIG. 5B, and FIG. 6.

It can be appreciated that the above described apparatus can be viewed as a method. In one exemplary embodiment, the method includes acquiring an emission map and an attenuation map, the emission map and the attenuation map each representing an initial image reconstruction of an object of a SPECT scan; calculating, using a radiative transfer equation method, a scatter source map of the object of the SPECT scan based on the emission map and the attenuation map; estimating scatter using the radiative transfer equation method and based on the scatter source map, the emission map, the attenuation map, and SPECT scanner related information; and performing image reconstruction of the object based on the scatter and raw data from the SPECT scan of the object.

Figure 3:
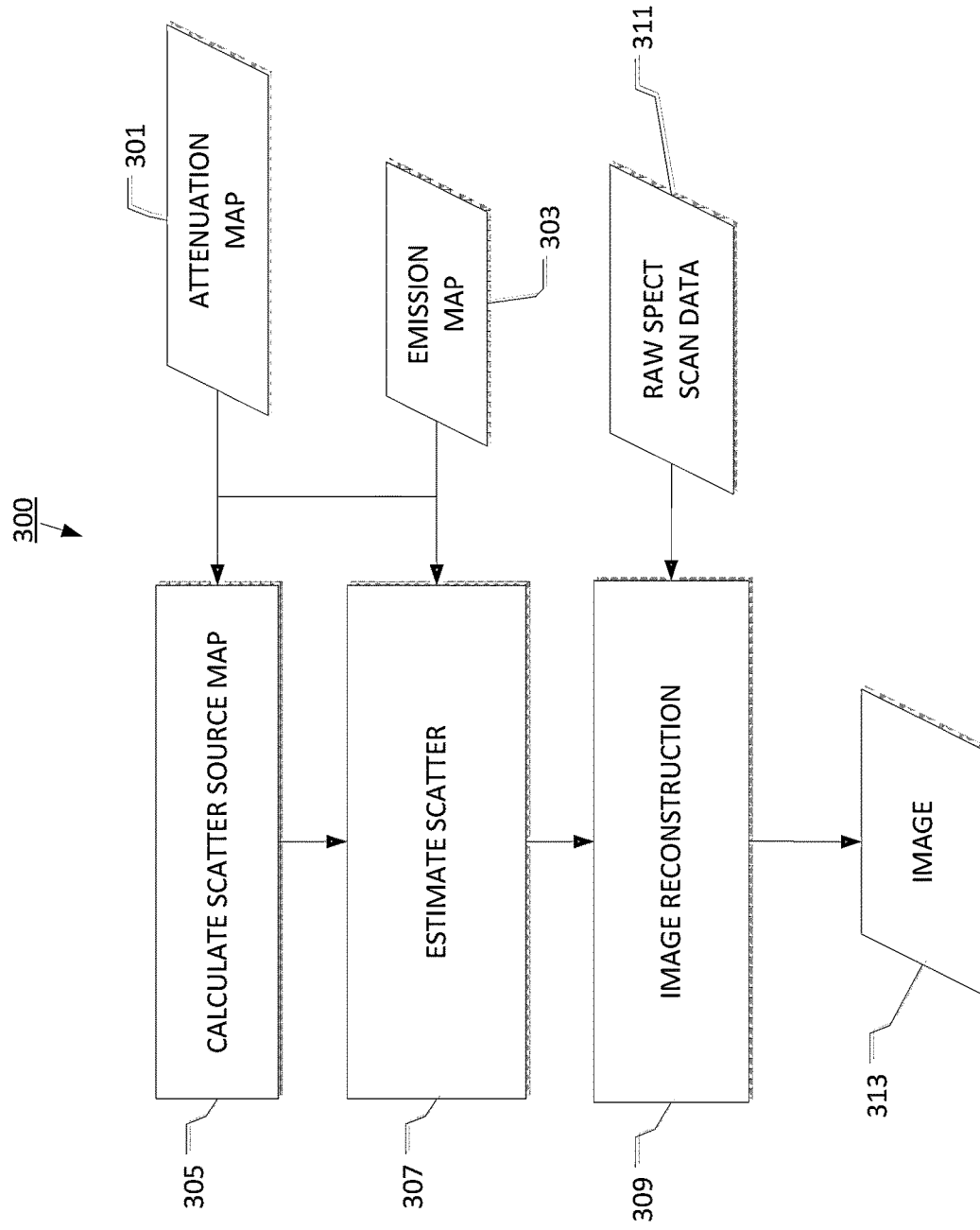
FIG. 3 is an algorithmic flowchart illustrating a method for removing scatter from detectors in a SPECT scan, according to one exemplary aspect of the present disclosure.
Figure 4:
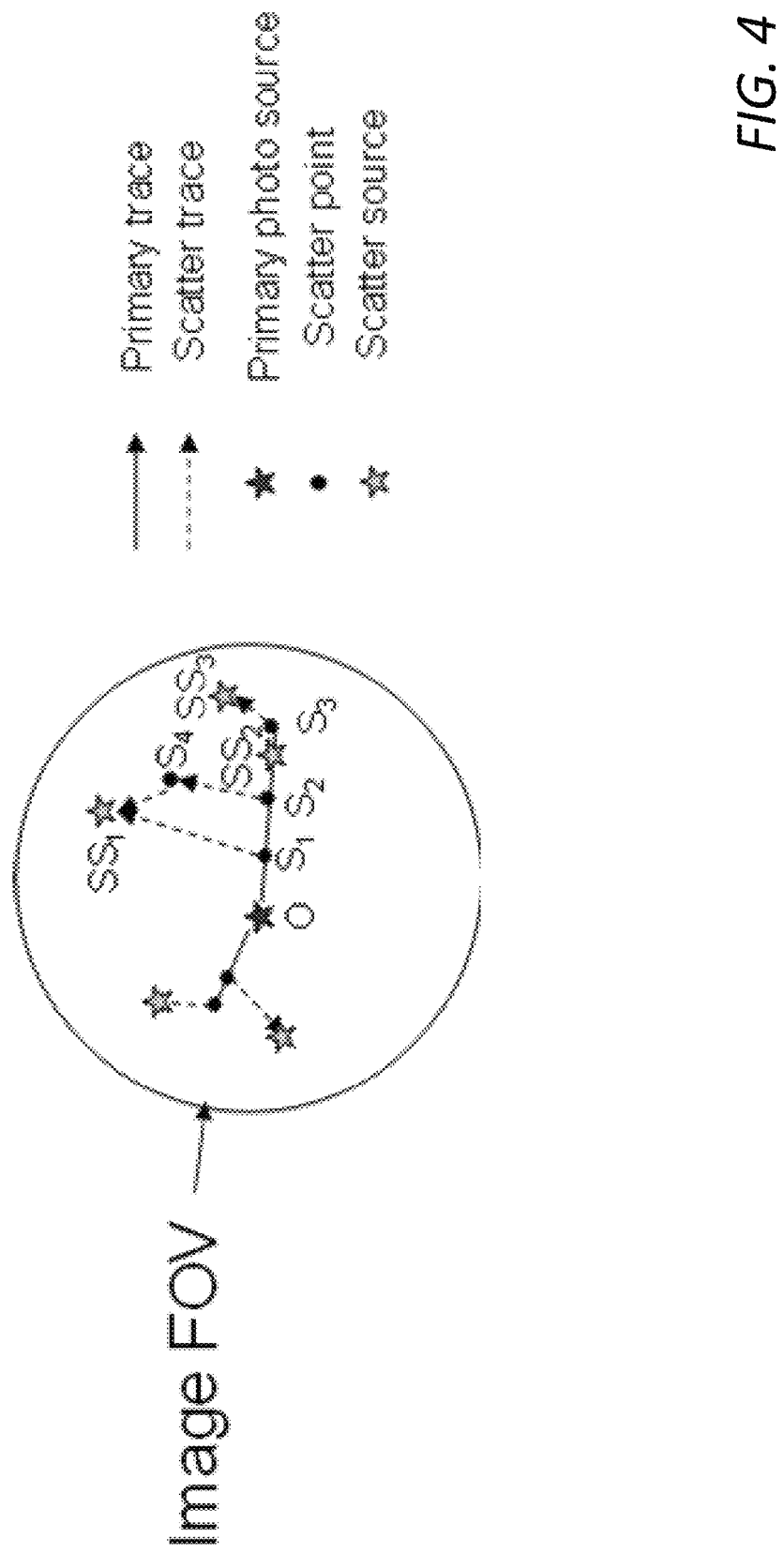
FIG. 4 shows a scatter source map, according to one exemplary aspect of the present disclosure.

FIG. 3 is a flow diagram of an exemplary method 300 for calculating scatter using the RTE method and reconstructing a SPECT image using the calculated scatter. The RTE method includes calculating a scatter source map (i.e. scatter cross-section map) and estimating scatter on detectors using the scatter source map.

In step 301, an attenuation map is acquired. The attenuation map (i.e. μ-map) can represent the spatial distribution of linear attenuation coefficients of an object in the SPECT scanner 1000 imaging field of view. In one exemplary embodiment, the attenuation map can be a transmission scan of the object performed by a separate CT scanner or CT scanner in a SPECT/CT scanner system. In another exemplary embodiment, the attenuation map is estimated from the emission map acquired by the SPECT scanner 1000 using techniques known by those of skill in the art.

In step 303, an emission map is acquired. The emission map may be an initial reconstruction of an object of a SPECT scan captured by the SPECT scanner 1000, or a 'coarse' reconstruction of the SPECT scan, thereby forming a basis from which scatter may be estimated. The emission map can include initial photon emission data (with scatter). The order of steps 301 and 303 can be interchangeable for other embodiments.

The ability to use dual and multiple tracer protocols is enabled in the present disclosure. Using the RTE-based approach enables the emission map to include information from multiple tracers at different energy windows. Additional discussion regarding the use of multiple tracers will be discussed later with reference to FIG. 6.

In step 305, a scatter source map is calculated. The scatter source map of the object OBJ is calculated using the RTE method, and it based on the attenuation map and emission acquired in steps 301 and 303, respectively. The scatter source map, an example of which is reflected in FIG. 4, may be calculated iteratively on the basis of a discretization of a SPECT scan volume, or cross-section thereof, wherein each discretized region of the SPECT scan volume may be considered a scatter source. The RTE method calculates the scatter source map (i.e. scatter cross-section map) iteratively with:

$$\psi_s(\vec{r}, E, \hat{\Omega}) = \int_{\vec{r}_{q0}}^{\vec{r}} d\vec{r}\, ' \int\!\!\int d\hat{\Omega}'\, dE'\, f(\vec{r}\,', E, E', \hat{\Omega}\cdot\hat{\Omega}') \\ [\psi_s(\vec{r}\,', E', \hat{\Omega}') + \psi_0(\vec{r}\,', E', \hat{\Omega}')] \exp[\int_{\vec{r}\,'}^{\vec{r}} d\vec{r}\,'' \mu(\vec{r}\,'', E)] \quad (2)$$

and $$\psi_0(\vec{r}, E, \hat{\Omega}) = q_0(\vec{r}_{q0}, E, \hat{\Omega}')\delta(\hat{\Omega}' - \hat{\Omega})\exp[- \int_{\vec{r}_{q0}}^{\vec{r}} d\vec{r}\,'' \mu(\vec{r}\,'', E)] \quad (3)$$

Equation 3 above can be used to determine the primary photo source (i.e. zero-order scatter). With equation 2 above, $\psi_s(\vec{r}, E, \hat{\Omega})$ is set to 0 and the first-order scatter in the volume is calculated. Subsequent iterations of the calculations may then be performed to obtain higher-order scatter points/sources according to the precision desired.

Figure 5A:
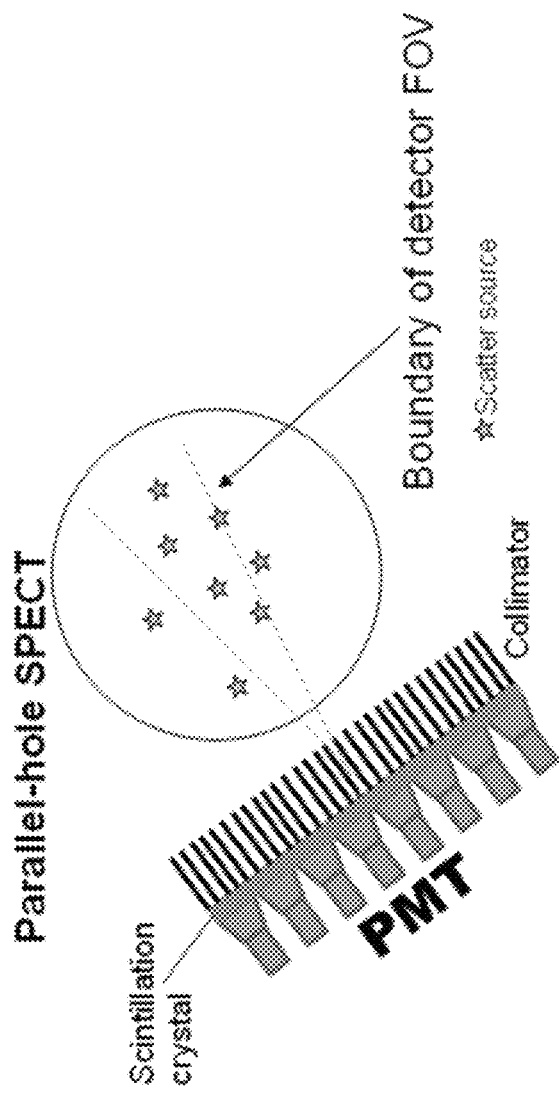
FIG. 5A shows a boundary of detector field of vision for a parallel collimator, according to one exemplary aspect of the present disclosure.
Figure 5B:
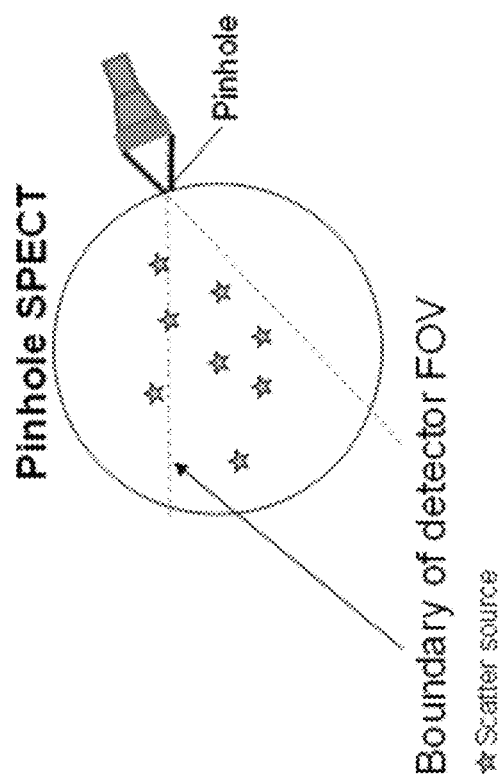
FIG. 5B shows a boundary of detector field of vision for a pinhole collimator, according to one exemplary aspect of the present disclosure.

In step 307, the scatter on detectors (e.g. 1005a, 1005b, 1005c) is calculated. The scatter is calculated using the scatter source map from step 305, the emission map from step 303, the attenuation map from step 301, and SPECT scanner related information. The SPECT scanner related information includes information on each detector's position and collimator type (e.g. parallel, pinhole). Because collimators can limit the path or trajectory of radiation events that can strike a particular detector crystal within any of the detectors, not all scatter on the scatter source map is within a particular detector crystal's field of vision (FOV). FIG. 5A shows an example of a particular detector crystal (i.e. scintillation crystal) and its boundary of detector FOV for a parallel collimator. Only the scatter on the scatter source map within the FOV will be considered a scatter source. Similarly, FIG. 5B shows a particular detector crystal and its boundary of detector FOV for a pinhole collimator, where only the scatter on the scatter source map within the boundary of detector FOV will be considered a scatter source. The RTE method calculates the detector response for each detector with:

$$\Phi_s(\vec{r}_D, E) = \\ \int\!\!\int d\hat{\Omega} R(E, \hat{\Omega}) \int_{\vec{r}_c}^{\vec{r}_D} d\vec{r}\,' \int\!\!\int d\hat{\Omega}'\, dE'\, f(\vec{r}\,', E, E', \hat{\Omega}\cdot\hat{\Omega}')[\psi_s(\vec{r}\,', E', \hat{\Omega}') + \\ \psi_0(\vec{r}\,', E', \hat{\Omega}')]\exp\left[-\int_{\vec{r}\,'}^{\vec{r}_D} d\vec{r}\,'' \mu(\vec{r}\,'', E)\right] \quad (4)$$

where $\Phi_s(\vec{r}_D, E)$ is the scatter flux on the detectors, $\vec{r}_D$ is the location of the detector, and R(E, $\hat{\Omega}$) is the factor corresponding to the parallel or pinhole collimator. Scatter events outside the detector FOV can be rejected. In other words, if a scatter source is within the boundary of detector FOV, R(E, $\hat{\Omega}$)=1. If a scatter source is outside the boundary of detector FOV, R(E, $\hat{\Omega}$)=0.

In step 309 of method 300, image reconstruction is performed to produce a final SPECT image 313. The image reconstruction is performed based on the scatter calculated from step 307 and raw SPECT data 311 from the SPECT scan of the object OBJ. In other words, the calculated scatter from step 307 is utilized, in view of raw SPECT scan data 311, for image reconstruction.

For analytical reconstruction (e.g. filtered backprojection), the calculated scatter for each detector crystal is deducted from the measured count value. For iterative reconstruction, the calculated scatter is incorporated into an iterative update equation. Without scatter, the iterative update equation is:

$$\bar{f}_j^{k+1} = \frac{\bar{f}_j^k}{\sum_i H_{ij}} \sum_i H_{ij} \frac{g_i}{\sum_{n=0}^{N-1} H_{in}\bar{f}_n^k} \quad (5)$$

where $g_i$ is the measured counts in ith LOR. $\bar{f}_j^k$ is the estimated activity in jth voxel at kth iteration.

In consideration of the scatter correction in iterative reconstruction, and the estimated scatter $s_i$ from the method described above, the iterative update equation with scatter correction will be:

$$\bar{f}_j^{k+1} = \frac{\bar{f}_j^k}{\sum_i H_{ij}} \sum_i H_{ij} \frac{g_i}{\sum_{n=0}^{N-1} H_{in}\bar{f}_n^k + s_i} \quad (6)$$

Figure 6:
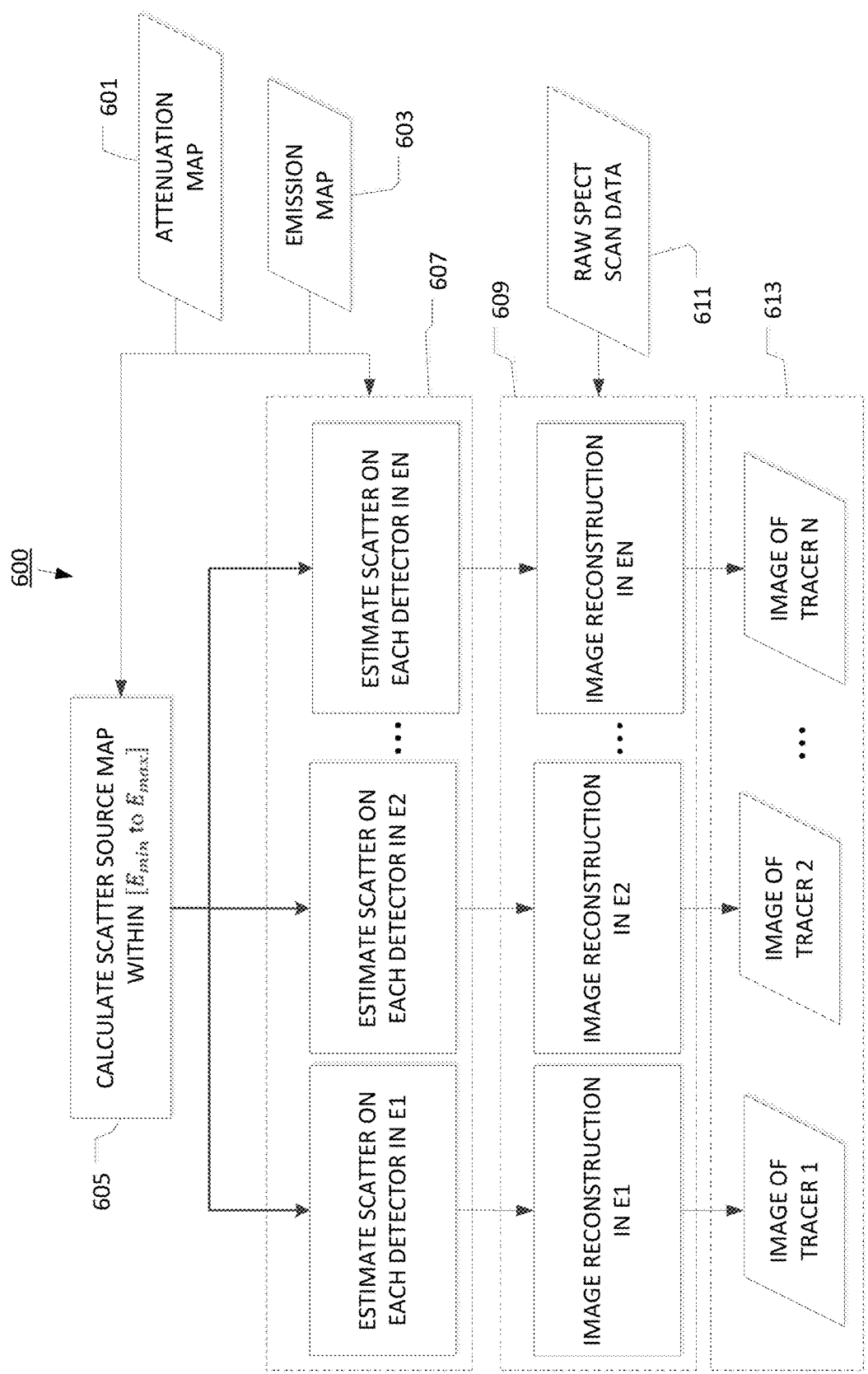
FIG. 6 is an algorithmic flowchart illustrating a method for removing scatter from detectors in a SPECT scan where multiple tracers are used, according to one exemplary aspect of the present disclosure.

The above mentioned techniques can also be used for multiple tracer scatter estimation using RTE, as shown in method 600 of FIG. 6. In this exemplary embodiment, there are N tracers, and each tracers is with different energy window E1, E2, . . . , EN. Among the energy widow, the minimum energy threshold is $E_{min}$, and the maximum energy threshold is $E_{max}$. Therefore, energy window [$E_{min}$ to $E_{max}$] will cover energy windows of all the tracers 1-N.

Step 601 is to acquire an attenuation map, and step 603 is to acquire an emission map. Steps 601 and 603 are similar to steps 301 and 303 respectively, which were described previously.

Step 605 is to calculate a scatter source map within the energy window [$E_{min}$ to $E_{max}$]. The scatter source map of the object OBJ is calculated using the RTE method described above, and it based on the attenuation map and emission acquired in steps 601 and 603, respectively. Step 605 is similar to step 305 described above, except the scatter source map includes scatter from energy window [$E_{min}$ to $E_{max}$].

Step 607 is to estimate scatter on each detector for E1 through EN. The scatter is calculated using the scatter source map from step 605, the emission map from step 603, the attenuation map from step 601, and SPECT scanner related information. The SPECT scanner related information includes information on each detector's position and collimator type (e.g. parallel, pinhole). Similar to step 307, equation 4 can be used to estimate scatter on each detector.

In step 609, image reconstruction is performed for E1 to EN to produce final SPECT images 613 for tracers 1-N. The image reconstruction is performed based on the scatter calculated from step 607 and raw SPECT data 611 from the SPECT scan of the object OBJ. Image reconstruction can be performed using any of the same techniques mentioned in step 309.

In conclusion, the present disclosure enables removing scatter from a SPECT image that is more accurate compared to energy-based methods, such as TEW. Furthermore, the present disclosure enables dual and multiple tracer protocols, compared to energy-based methods. Lastly, the present disclosure enables first-order and higher-order scatter to be estimated while keeping the computational burden much lower.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

Embodiments of the present disclosure may also be as set forth in the following parentheticals.

(1) An apparatus for reconstructing an image in a single photon emission computed tomography (SPECT) scanner, comprising: processing circuitry configured to acquire an emission map and an attenuation map, the emission map and the attenuation map each representing an initial image reconstruction of an object of a SPECT scan, calculate, using a radiative transfer equation method, a scatter source map of the object of the SPECT scan based on the emission map and the attenuation map, estimate scatter using the radiative transfer equation method and based on the scatter source map, the emission map, the attenuation map, and SPECT scanner related information, and perform image reconstruction of the object based on the scatter and raw data from the SPECT scan of the object.

(2) The apparatus of (1), wherein the scatter source map includes contributions from first-order scatter and higher-order scatter.

(3) The apparatus of any (1) to (2), wherein the scatter includes contributions from first-order scatter and higher-order scatter.

(4) The apparatus of any (1) to (3), wherein the SPECT scanner related information includes position information of one or more detectors mounted on the SPECT scanner for scanning the object, and a collimator type of the one or more detectors, the collimator type being parallel or pinhole.

(5) The apparatus of any (1) to (4), wherein the image reconstruction is performed iteratively.

(6) The apparatus of any (1) to (5), where the image reconstruction is performed using filtered back projection.

(7) The apparatus of any (1) to (6), wherein the attenuation map is based on a computed tomography scan of the object.

(8) The apparatus of any (1) to (7), wherein multiple tracers are used in the object for the SPECT scan.

(9) A method for reconstructing an image in a single photon emission computed tomography (SPECT) scanner, comprising: acquiring an emission map and an attenuation map, the emission map and the attenuation map each representing an initial image reconstruction of an object of a SPECT scan; calculating, using a radiative transfer equation method, a scatter source map of the object of the SPECT scan based on the emission map and the attenuation map; estimating scatter using the radiative transfer equation method and based on the scatter source map, the emission map, the attenuation map, and SPECT scanner related information; and performing image reconstruction of the object based on the scatter and raw data from the SPECT scan of the object.

(10) The method of (9), wherein the scatter source map includes contributions from first-order scatter and higher-order scatter.

(11) The method of any (9) to (10), wherein the scatter includes contributions from first-order scatter and higher-order scatter.

(12) The method of any (9) to (11), wherein the SPECT scanner related information includes position information of one or more detectors mounted on the SPECT scanner for scanning the object, and a collimator type of the one or more detectors, the collimator type being parallel or pinhole.

(13) The method of any (9) to (12), wherein the image reconstruction is performed iteratively.

(14) The method of any (9) to (13), where the image reconstruction is performed using filtered back projection.

(15) The method of any (9) to (14), wherein the attenuation map is based on a computed tomography scan of the object.

(16) The method of any (9) to (15), wherein multiple tracers are used in the object for the SPECT scan.

(17) A non-transitory computer-readable storage medium storing computer-readable instructions that, when executed by a computer, cause the computer to perform a method comprising: acquiring an emission map and an attenuation map, the emission map and the attenuation map each representing an initial image reconstruction of an object of a SPECT scan; calculating, using a radiative transfer equation method, a scatter source map of the object of the SPECT scan based on the emission map and the attenuation map; estimating scatter using the radiative transfer equation method and based on the scatter source map, the emission map, the attenuation map, and SPECT scanner related information; and performing image reconstruction of the object based on the scatter and raw data from the SPECT scan of the object.

(18) The non-transitory computer-readable storage medium of (17), wherein the scatter source map includes contributions from first-order scatter and higher-order scatter.

(19) The non-transitory computer-readable storage medium of any (17) to (18), wherein the scatter includes contributions from first-order scatter and higher-order scatter.

(20) The non-transitory computer-readable storage medium of any (17) to (19), wherein multiple tracers are used in the object for the SPECT scan.

The invention claimed is:

1. An apparatus for reconstructing an image in a single photon emission computed tomography (SPECT) scanner, comprising:
processing circuitry configured to
acquire an emission map and an attenuation map, the emission map and the attenuation map each representing an initial image reconstruction of an object of a SPECT scan,
calculate, using a radiative transfer equation method, a scatter source map of the object of the SPECT scan based on the emission map and the attenuation map,
estimate scatter using the radiative transfer equation method and based on the scatter source map, the emission map, the attenuation map, and SPECT scanner related information, wherein the SPECT scanner related information includes position information of the SPECT scanner's field of view (FOV), and
perform image reconstruction of the object based on the estimated scatter and raw data from the SPECT scan of the object.

2. The apparatus of claim 1, wherein the scatter source map calculated by the processing circuitry includes contributions from first-order scatter and higher-order scatter.

3. The apparatus of claim 1, wherein the estimated scatter estimated by the processing circuitry includes contributions from first-order scatter and higher-order scatter.

4. The apparatus of claim 1, wherein the SPECT scanner related information used by the processing circuitry includes position information of one or more detectors mounted on the SPECT scanner for scanning the object, and a collimator type of the one or more detectors, the collimator type being parallel or pinhole.

5. The apparatus of claim 1, wherein the processing circuitry is further configured to perform the image reconstruction iteratively.

6. The apparatus of claim 1, where the processing circuitry is further configured to perform the image reconstruction using filtered back projection.

7. The apparatus of claim 1, wherein the attenuation map acquired by the processing circuitry is based on a computed tomography scan of the object.

8. The apparatus of claim 1, wherein multiple tracers are used in the object for the SPECT scan.

9. A method for reconstructing an image in a single photon emission computed tomography (SPECT) scanner, comprising:
acquiring an emission map and an attenuation map, the emission map and the attenuation map each representing an initial image reconstruction of an object of a SPECT scan;
calculating, using a radiative transfer equation method, a scatter source map of the object of the SPECT scan based on the emission map and the attenuation map;
estimating scatter using the radiative transfer equation method and based on the scatter source map, the emission map, the attenuation map, and SPECT scanner related information, wherein the SPECT scanner related information includes position information of the SPECT scanner's field of view (FOV); and
performing image reconstruction of the object based on the estimated scatter and raw data from the SPECT scan of the object.

10. The method of claim 9, wherein the scatter source map includes contributions from first-order scatter and higher-order scatter.

11. The method of claim 9, wherein the estimated scatter includes contributions from first-order scatter and higher-order scatter.

12. The method of claim 9, wherein the SPECT scanner related information includes position information of one or more detectors mounted on the SPECT scanner for scanning the object, and a collimator type of the one or more detectors, the collimator type being parallel or pinhole.

13. The method of claim 9, wherein the performing step further comprises performing the image reconstruction iteratively.

14. The method of claim 9, wherein the performing step further comprises performing the image reconstruction using filtered back projection.

15. The method of claim 9, wherein the attenuation map is based on a computed tomography scan of the object.

16. The method of claim 9, wherein multiple tracers are used in the object for the SPECT scan.

17. A non-transitory computer-readable storage medium storing computer-readable instructions that, when executed by a computer, cause the computer to perform a method comprising:
acquiring an emission map and an attenuation map, the emission map and the attenuation map each representing an initial image reconstruction of an object of a SPECT scan;
calculating, using a radiative transfer equation method, a scatter source map of the object of the SPECT scan based on the emission map and the attenuation map;
estimating scatter using the radiative transfer equation method and based on the scatter source map, the emission map, the attenuation map, and SPECT scanner related information, wherein the SPECT scanner related information includes position information of the SPECT scanner's field of view (FOV); and
performing image reconstruction of the object based on the estimated scatter and raw data from the SPECT scan of the object.

18. The non-transitory computer-readable storage medium of claim 17, wherein the scatter source map includes contributions from first-order scatter and higher-order scatter.

19. The non-transitory computer-readable storage medium of claim 17, wherein the scatter includes contributions from first-order scatter and higher-order scatter.

20. The non-transitory computer-readable storage medium of claim 17, wherein multiple tracers are used in the object for the SPECT scan.

* * * * *